United States Patent [19]

Simonnet

[11] Patent Number: 6,120,778

[45] Date of Patent: *Sep. 19, 2000

[54] TRANSPARENT NANOEMULSION BASED ON SILICONE SURFACTANTS AND USE IN COSMETICS OR IN DERMOPHARMACEUTICALS

[75] Inventor: Jean-Thierry Simonnet, Paris, France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/772,724

[22] Filed: Dec. 23, 1996

[30] Foreign Application Priority Data

Dec. 21, 1995 [FR] France .................................. 95 15291

[51] Int. Cl.⁷ ...................................................... A61K 7/00
[52] U.S. Cl. ..................... 424/401; 424/70.1; 424/70.12; 424/450; 514/938
[58] Field of Search ................................... 424/401, 450, 424/70.1, 70.12; 514/938

[56] References Cited

U.S. PATENT DOCUMENTS

| | | |
|---|---|---|
| 5,364,633 | 11/1994 | Hill et al. . |
| 5,919,487 | 7/1999 | Simonnet et al. . |
| 5,958,433 | 9/1999 | Simonnet . |

FOREIGN PATENT DOCUMENTS

| | | |
|---|---|---|
| 0 226 337 A1 | 6/1987 | European Pat. Off. . |
| 0 330 369 A1 | 8/1989 | European Pat. Off. . |
| 0 406 162 A3 | 1/1991 | European Pat. Off. . |
| 0 407 089 A3 | 1/1991 | European Pat. Off. . |
| 0 514 934 A1 | 11/1992 | European Pat. Off. . |
| 0 529 847 A1 | 3/1993 | European Pat. Off. . |
| 0 559 013 A1 | 9/1993 | European Pat. Off. . |
| 0 579 455 A1 | 1/1994 | European Pat. Off. . |
| 0 615 741 | 9/1994 | European Pat. Off. . |
| 615741 | 9/1994 | European Pat. Off. . |
| 0 631 774 A1 | 1/1995 | European Pat. Off. . |
| 0 638 308 A1 | 2/1995 | European Pat. Off. . |
| 638308 | 2/1995 | European Pat. Off. . |
| 2 315 991 | 1/1977 | France . |
| 2 597 345 A1 | 10/1987 | France . |
| 2 597 367 A1 | 10/1987 | France . |
| 2 683 453 | 5/1993 | France . |
| 2 693 466 | 1/1994 | France . |
| 1-293131 | 11/1989 | Japan . |
| 7-291825 | 11/1995 | Japan . |

OTHER PUBLICATIONS

Tenside Surfactants Detergents, vol. 29, No. 2, Mar. 29, 1992, pp. 78–83, B. Gruening, et al.
Patent Abstracts of Japan, JP 01–293131, Nov. 27, 1989.
Patent Abstracts of Japan, JP 07–291825, Nov. 7, 1995.

*Primary Examiner*—Thurman K. Page
*Assistant Examiner*—Brian K. Seidleck
*Attorney, Agent, or Firm*—Oblon, Spivak, McClelland, Maier & Neustadt, P.C.

[57] ABSTRACT

The present application relates to a transparent oil-in-water emulsion, the oil globules of which have a mean size of less than 100 nm, which comprises at least one silicone surfactant. The emulsion according to the invention is stable on storage and can contain significant amounts of oil while retaining good transparency. It can contain heat-sensitive active principles and can be used in particular in the cosmetics field and in dermatology for the treatment and the care of the skin, mucous membranes, nails, scalp and hair.

34 Claims, No Drawings

TRANSPARENT NANOEMULSION BASED ON SILICONE SURFACTANTS AND USE IN COSMETICS OR IN DERMOPHARMACEUTICALS

This application claims priority of French patent application 95-15291, filed Dec. 21, 1995.

BACKGROUND OF THE INVENTION

1. Field of the Invention

The present invention relates to an oil-in-water emulsion, in particular a transparent oil-in-water emulsion, the oil globules of which have a mean size of less than 100 nm, which comprises at least one silicone surfactant.

The present invention further relates to use of such an oil-in-water emulsion in topical application, in particular in the cosmetic and dermatological fields.

1. Discussion of the Background

Oil-in-water emulsions, wherein an oily phase is dispersed in an aqueous phase, are well-known in the field of cosmetics and in dermopharmaceuticals, in particular for the preparation of products such as lotions, skin tonics, serums, creams or eaux de toilette.

Emulsions comprising oil globules having a mean size of less than 100 nm are known as nanoemulsions. Such emulsions have been used to obtain transparent compositions having an appearance similar to that of water and resulting in a feel similar to that of a cream or a milk after application to the skin.

Thus, EP-A-406,162 describes nanoemulsions comprising an amphiphilic lipid phase comprising phosphoglycerides. These nanoemulsions are obtained by a high-pressure homogenization process. The nanoemulsions exhibit the disadvantage of being unstable on storage at conventional storage temperatures, i.e., between 0 and 45° C., and for this reason provide yellow compositions producing rancid smells which develop after storage for a few days.

Moreover, EP-A-615,741 describes nanoemulsions comprising the combination of a long-chain fatty alcohol and/or fatty acid and a surfactant of the long-chain fatty acid soap type, forming a gel with a phase transition temperature greater than 60° C. These nanoemulsions are prepared at high temperatures, greater than 70° C., which makes it impossible to use heat-sensitive active principles (for example vitamins) in such compositions.

Accordingly, an object of the present invention is to provide a nanoemulsion which does not exhibit the disadvantages encountered with those known to date.

Yet another object of the invention is to provide a method for the cosmetic treatment of the skin, mucous membranes, nails, scalp, and/or hair.

Yet another object of the invention is to provide a method for the preparation of a composition intended for the dermatological treatment of diseases of the skin, mucous membranes, nails, scalp, and/or hair.

Yet another object of the invention is to provide a method for the therapeutic and/or non-therapeutic treatment of the skin, mucous membranes, nails, scalp, and/or hair.

SUMMARY OF THE INVENTION

The nanoemulsion according to the invention truly makes it possible to overcome the problems mentioned above. Applicant has surprisingly found that it was possible to obtain a stable nanoemulsion which can be prepared at temperatures between 20 and 45° C. by using a specific surfactant.

The present invention provides an oil-in-water emulsion comprising an oily phase dispersed in an aqueous phase, the oil globules of which have a mean size of less than 100 nm, wherein the oil-in-water emulsion comprises at least one silicone surfactant.

The emulsions in accordance with the invention, the oil globules of which have a mean size of less than 100 nm, are stable on storage between 0 and 45° C. after at least two months. They are prepared at temperatures between 20 and 45° C.; it is therefore possible to introduce heat-sensitive active principles therein, for example vitamins and vegetable oils containing unsaturated fatty acids, without the risk of these active principles being degraded.

Moreover, the emulsions according to the invention can contain significant amounts of oil while retaining good transparency properties. Further, they promote the penetration of the active principles into the surface layers of the skin.

A silicone surfactant is a silicone compound having at least an oxyethylenated and/or oxypropylenated chain. Examples of silicone surfactants which can be used according to the present invention include, but are not limited to those described in U.S. Pat. No. 5,364,633 and U.S. Pat. No. 5,411,744, which are both incorporated in their entirety herein by reference.

DETAILED DESCRIPTION OF THE PREFERRED EMBODIMENTS

The silicone surfactant used according to the present invention is preferably a compound of formula (I):

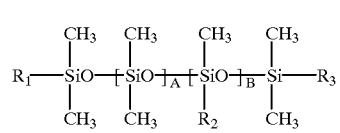

(I)

wherein:

R$_1$, R$_2$ and R$_3$, independently of one another, represent C$_1$-C$_6$ alkyl or —(CH$_2$)$_x$—(OCH$_2$CH$_2$)$_y$—(OCH$_2$CH$_2$CH$_2$)$_z$—OR$_4$ wherein:

at least one of R$_1$, R$_2$ or R$_3$ is not alkyl,

R$_4$ is hydrogen, alkyl or acyl, x is an integer ranging from 1 to 6, y is an integer ranging from 1 to 30, and z is an integer ranging from 0 to 5;

A is an integer ranging from 0 to 200; and

B is a integer ranging from 0 to 50, with the proviso that A and B are not simultaneously zero.

In the compound of formula (I), the alkyl radical is preferably a methyl radical, x is preferably an integer ranging from 2 to 6, and y is preferably an integer ranging from 4 to 30.

Examples of silicone surfactants of formula (I) are compounds of formula (II):

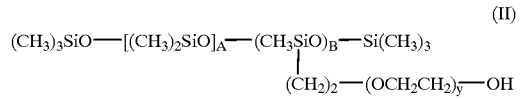

(II)

wherein:

A is an integer ranging from 20 to 105,

B is an integer ranging from 2 to 10, and y is an integer ranging from 10 to 20.

Further examples of silicone surfactants of formula (I), are compounds of formula (III):

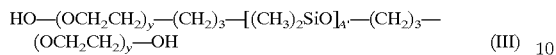

wherein A' and y are integers ranging from 10 to 20.

Suitable compounds of the invention are those sold by the company Dow Corning under the names DC 5329, DC 7439-146, DC 2-5695, and Q4-3667. Compounds DC 5329, DC 7439-146, and DC 2-5695 are compounds of formula (II) wherein:

for DC 5329, A is 22, B is 2 and y is 12;

for DC 7439-146, A is 103, B is 10 and y is 12; and for DC 2-5695, A is 27, B is 3 and y is 12.

Compound Q4-3667 is a compound of formula (III) wherein A is 15 and y is 13.

Preferably, the ratio by weight of the amount of oily phase contained in the emulsion to the amount of silicone surfactant preferably varies from 2 to 10, more preferably from 3 to 6.

Preferably, the amount of silicone surfactant in the emulsion according to the invention ranges from 1 to 15% by weight, more preferably from 3 to 6%, still more preferably 4 to 5% by weight with respect to the total weight of the emulsion.

Preferably, the emulsion in accordance with the invention contains an amount of oily phase ranging from 5 to 40% by weight, more preferably 10 to 30% by weight with respect to the total weight of the emulsion.

Examples of oils which can be used in the invention include, but are not limited to mineral oils (liquid petrolatum), vegetable oils (liquid fraction of karite butter, sunflower oil), animal oils (perhydrosqualene), synthetic oils (purcellin oil), natural or synthetic essential oils (oils of eucalyptus, of lavandin, of lavender, of vetiver, of Litsea cubeba, of lemon, of sandalwood, of rosemary, of camomile, of savory, of nutmeg, of cinnamon, of hyssop, of caraway, of orange, of geraniol, of cade and of bergamot), volatile silicone oils (decamethylcyclopentasiloxane) or non-volatile silicone oils (dodecamethylcyclohexasiloxane), fluorinated oils (perfluoropolyethers) or halogenated hydrocarbons (fluorocarbons, such as fluoroamines, e.g., perfluorotributylamine, or fluorinated hydrocarbons, e.g., perfluorodecahydronaphthalene). Fatty substances may also be used, e.g., fatty alcohols, fatty acids, waxes or gums (e.g., silicone gum).

According to a specific embodiment of the invention, the emulsion in accordance with the invention further contains one or a number of ionic amphiphilic lipids.

The ionic amphiphilic lipids used in the nanoemulsions of the invention are preferably chosen from the group formed by neutralized anionic lipids, amphoteric ionic lipids or alkylsulphonic derivatives.

The ionic amphiphilic lipids are more preferably chosen from:

alkaline salts of dicetyl and dimyristyl phosphate;

alkaline salts of cholesterol sulphate;

alkaline salts of cholesterol phosphate;

lipoamino acids, such as mono- and disodium acylglutamates;

sodium salts of phosphatidic acid;

phospholipids;

alkylsulphonic derivatives of formula:

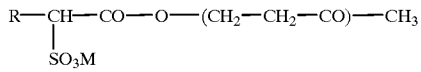

wherein:

R represents $C_{16}$–$C_{22}$ alkyl radicals, in particular the $C_{16}H_{33}$ and $C_{18}H_{37}$ radicals, taken as a mixture or separately, and M is an alkali metal, such as sodium and potassium; and mixtures thereof.

Preferred ionic amphiphilic lipids are the monosodium salt of N-stearoylglutamic acid, sold under the name "acylglutamate HS 21" by the company Ajinomoto, sodium dicetyl phosphate, and sodium dimyristyl phosphate.

Preferably, the ionic amphiphilic lipids are present at concentrations ranging from 0 to 20% by weight, more preferably from 5 to 15%, still more preferably from 9 to 12% by weight with respect to the weight of silicone surfactant.

The emulsion in accordance with the present invention can contain additives for improving the transparency of the formulation.

These additives can be chosen, for example, from:

lower $C_1$-$C_8$ alcohols, such as ethanol;

glycols, such as glycerol, propylene glycol, 1,3-butylene glycol, dipropylene glycol or polyethylene glycols containing from 4 to 16, preferably from 8 to 12 ethylene oxide units;

and mixtures thereof.

The additives such as those mentioned above are used in the emulsions of the invention preferably at concentrations ranging from 0 to 30% by weight, more preferably in a concentration greater than 5% by weight with respect to the total weight of the emulsion.

The alcohols are preferably used at concentrations ranging from 5 to 20% by weight with respect to the total weight of the emulsion.

The glycols are preferably used at concentrations ranging from 5 to 15% by weight.

Further, the use of the alcohols as defined above at concentrations greater than or equal to 15% by weight makes it possible to obtain preservative-free emulsions.

The oil globules of the emulsions of the invention preferably have a mean size ranging from 15 to 100 nm, more preferably from 15 to 90 nm, still more preferably from 45 to 75 nm. The decrease in the size of the globules makes it possible to promote the penetration of the active principles into the surface layers of the skin (vehicle effect) and to improve the transparency of the emulsion.

The emulsions according to the invention are colourless and possibly slightly bluish and exhibit a transparency, determined by the coefficient of transmittance measured at a wavelength of 600 nm, preferably ranging from 30 to 90%, more preferably from 50 to 80%.

The process for obtaining the emulsions according to the invention comprises the following steps:

a) the aqueous phase and the oily phase are mixed, with vigorous stirring, at an ambient temperature of less than 45° C., preferably less than 30° C.; and b) high-pressure homogenization is carried out at a pressure greater than $10^8$ Pa, preferably ranging from $12\times10^7$ to $18\times10^7$ Pa.

Such a process makes it possible to produce, at ambient temperature, nanoemulsions which are compatible with heat-sensitive active compounds. Moreover, these nanoemulsions can contain significant amounts of oils, in particular fragrances which contain fatty substances, without denaturing them.

For topical application, the emulsion according to the invention preferably contains a cosmetically and/or dermatologically and/or pharmaceutically acceptable medium.

The emulsion of the invention may be used for the cosmetic treatment of the skin, mucous membranes, nails, scalp, and/or hair, as well as for the preparation of a composition intended for the dermatological treatment of diseases of the skin, mucous membranes, nails, scalp, and/or hair.

The invention may be used for the therapeutic and/or non-therapeutic treatment of the skin, mucous membranes, nails, scalp, and/or hair, by appling the emulsion defined above to the skin, mucous membranes, nails, scalp, and/or hair.

The emulsion in particular makes possible good moisturization of the skin and the treatment of greasy skin and of sensitive skin. The present invention consequently also relates to the use of the emulsion defined above for moisturizing the skin and/or treating greasy skin and/or treating sensitive skin. A definition of sensitive skin is provided in EP-A-680,749, the entire contents of which are incorporated herein by reference.

The emulsion according to the invention can in particular be provided in lotion, serum, or gel form and can contain the adjuvants commonly used in the fields under consideration, e.g., gelling agents, preservatives, antioxidants, fragrances, fillers, coloring materials, and lipid vesicles.

The emulsion according to the invention can in particular constitute cleansing, protective, treatment or care compositions for the face, neck, hands, nails, or body (e.g., cleansing milk, make-up removal milk, or body milk), artificial tanning compositions, or compositions for the bath or shower.

The emulsion according to the invention can also constitute shampoos, hair-setting lotions, treating lotions, styling creams or gels, dyeing compositions, or lotions or gels for combating hair loss.

The emulsion according to the invention can contain water-soluble or fat-soluble active principles having a cosmetic or dermatological activity. The fat-soluble active principles are in the oily globules of the emulsion, whereas the water-soluble active principles are in the aqueous phase of the emulsion. Examples of fat-soluble active principles are retinol (vitamin A) and its derivatives, such as retinol palmitate.

Other features of the invention will become apparent in the course of the following descriptions of exemplary embodiments which are given for illustration of the invention and are not intended to be limiting thereof.

EXAMPLES

For these examples, the following procedure is used:

a) in a first phase A, the mixture of the constituents is homogenized at a temperature of 45° C.;

b) in a second phase B, the hydrophilic adjuvants and active principles are dissolved at a temperature of 20 to 30° C.; and c) the phases A and B are then mixed using a propeller homogenizer and then homogenization is carried out using a high-pressure homogenizer of the Soavi-Niro type at a pressure of 1500 bars, with 7 passes, the temperature of the product being maintained below 30° C.

If ethanol is present in the composition, it is added to the phase A just before addition of the latter to the phase B.

In the Examples below, "q.s. for 100%" means a quantity sufficient to total 100%. All percentages are given as percent by weight, unless otherwise indicated.

EXAMPLE 1
Care Fluid for Greasy Skin

| First phase: | |
|---|---|
| Silicone surfactant (DC 2-5695) | 5% |
| Dodecamethylcyclohexasiloxane | 6% |
| Decamethylcyclopentasiloxane | 6% |
| Silicone gum (Q2-1403 sold by Dow Corning) | 3% |
| Non-denatured absolute ethanol | 15% |
| Second phase: | |
| Glycerol | 5% |
| Demineralized water | q.s. for 100% |

A transparent emulsion is obtained, the oil globules of which have a size of 52 nm, with a transparency, determined by the coefficient of transmittance at 600 nm, of 80%.

This fluid emulsion is cool on application.

EXAMPLE 2
Care Fluid for Sensitive Skin

| First phase: | |
|---|---|
| Silicone surfactant (DC 2-5695) | 5% |
| Decamethylcyclopentasiloxane | 6% |
| Perhydrosqualene | 6% |
| Silicone gum (Q2-1403 sold by Dow Corning) | 3% |
| Second phase: | |
| Glycerol | 5% |
| Dipropylene glycol | 10% |
| Demineralized water | q.s. for 100% |

An opalescent emulsion is obtained, the globules of which have a size of 70 nm, with a transparency of 40%.

This fluid emulsion is pleasant on application and suitable for treating sensitive skin.

EXAMPLE 3
Day Care Fluid

| First phase: | |
|---|---|
| Silicone surfactant (DC 2-5695) | 4.5% |
| Disodium salt of N-stearoyl-L-glutamic acid, sold under the name Acylglutamate HS21 by the Company Ajinomoto (ionic amphiphilic lipid) | 0.5% |
| Cyclomethicone | 6 |
| Jojoba oil | 6 |
| Avocado oil | 3 |
| Retinol palmitate | 0.3% |
| Non-denatured absolute ethanol | 15 |
| Second phase: | |

-continued

| | |
|---|---|
| Glycerol | 5 |
| Demineralized water | q.s. for 100 |

A transparent emulsion is obtained, the globules of which have a size of 57 nm, with a transparency of 67%.

This fluid emulsion is suitable for treating the skin.

This application is based on French Patent Application 95-15291, filed with the French Patent Office on Dec. 21, 1995, the entire contents of which are incorporated herein by reference.

Obviously, numerous modifications and variations of the present invention are possible in light of the above teachings. It is therefore to be understood that within the scope of the appended claims, the invention may be practices otherwise than as specifically described herein.

What is claimed as new and desired to be secured by: Letters Patent of the United States is:

1. An oil-in-water emulsion, comprising an oily phase dispersed in an aqueous phase, wherein said oily phase comprises oil globules having a mean size of less than 100 nm, and wherein said oil-in-water emulsion comprises at least one silicone surfactant represented by formula (I):

$$R_1-\underset{\underset{CH_3}{|}}{\overset{\overset{CH_3}{|}}{Si}}O-[\underset{\underset{CH_3}{|}}{\overset{\overset{CH_3}{|}}{Si}}O]_A-[\underset{\underset{R_2}{|}}{\overset{\overset{CH_3}{|}}{Si}}O]_B-\underset{\underset{CH_3}{|}}{\overset{\overset{CH_3}{|}}{Si}}-R_3 \quad (I)$$

wherein:

$R_1 R_2$, and $R_3$, independently of one another, represent $C_1$–$C_6$ alkyl or $-(CH_2)_x-(OCH_2CH_2)_y-(OCH_2CH_2CH_2)_z-OR_4$ at least one of $R_1$, $R_2$ and $R_3$ is not alkyl, $R_4$ is hydrogen, alkyl or acyl, x is an integer ranging from 1 to 6, y is an integer ranging from 1 to 30, and z is an integer ranging from 0 to 5;

A is an integer ranging from 0 to 200; and

B is an integer ranging from 0 to 50, with the proviso that A and B are not simultaneously zero; and wherein said oil globules comprise an oil selected from the group consisting of mineral oils, vegetable oils, animal oils, synthetic oils, essential oils, silicone oils, fluorinated oils halogenated hydrocarbons, fatty alcohols, fatty acids, waxes, and gums, and wherein the ratio of the oily phase to the silicone surfactant is from 2 to 10.

2. The emulsion of claim 1, wherein the silicone surfactant is a compound of formula (I) where the alkyl radical is a methyl radical, x is an integer ranging from 2 to 6 and y is an integer ranging from 4 to 30.

3. The emulsion of claim 1, wherein the silicone surfactant is a compound of formula (II):

$$(CH_3)_3SiO-[(CH_3)_2SiO]_A-(CH_3\underset{\underset{(CH_2)_2-(OCH_2CH_2)_y-OH}{|}}{Si}O)_B-Si(CH_3)_3 \quad (II)$$

wherein A is an integer ranging from 20 to 105, B is an integer ranging from 2 to 10, and y is an integer ranging from 10 to 20.

4. The emulsion of claim 3, wherein:

A is 22, B is 2, and y is 12;

A is 103, B is 10, and y is 12; or

A is 27, B is 3, and y is 12.

5. The emulsion of claim 1, wherein the silicone surfactant is a compound of formula (III):

$$HO-(OCH_2CH_2)_y-(CH_2)_3-[(CH_3)_2SiO]_{A'}-(CH_2)_3-(OCH_2CH_2)_y-OH \quad (III)$$

wherein A' and y are integers ranging from 10 to 20.

6. The emulsion of claim 5, wherein the silicone surfactant is a compound of formula (III), wherein A is 15 and y is 13.

7. The emulsion of claim 1, wherein the amount of silicone surfactant ranges from 1 to 15% by weight with respect to the total weight of the emulsion.

8. The emulsion of claim 1, wherein the amount of silicone surfactant ranges from 3 to 6% by weight with respect to the total weight of the emulsion.

9. The emulsion of claim 1, wherein the oily phase is present in an amount ranging from 5 to 40% by weight with respect to the total weight of the emulsion.

10. The emulsion of claim 1, wherein the oily phase is present in an amount ranging from 10 to 30% by weight with respect to the total weight of the emulsion.

11. The emulsion of claim 1, further comprising at least one ionic amphiphilic lipid.

12. The emulsion of claim 13, wherein the ionic amphiphilic lipid is selected from the group consisting of neutralized anionic lipids, amphoteric ionic lipids, alkylsulphonic derivatives, and mixtures thereof.

13. The emulsion of claim 11, wherein the ionic amphiphilic lipid is selected from the group consisting of:

alkaline salts of dicetyl and dimyristyl phosphate;

alkaline salts of cholesterol sulphate;

alkaline salts of cholesterol phosphate;

salts of lipoamino acids;

sodium salts of phosphatidic acid;

phospholipids;

alkylsulphonic derivatives of formula:

$$R-\underset{\underset{SO_3M}{|}}{CH}-CO-O-(CH_2-CH_2-CO)-CH_3$$

wherein R represents $C_{16}$–$C_{22}$ alkyl radicals, taken as a mixture or separately, and M is an alkali metal; and mixtures thereof.

14. The emulsion of claim 11, wherein the ionic amphiphilic lipid is present in concentrations ranging from 5 to 15% by weight with respect to the weight of silicone surfactant.

15. The emulsion of claim 14, wherein the oily phase comprises at least one silicone oil and/or one silicone gum.

16. The emulsion of claim 14, wherein the size of the oily globules is such that the emulsion is transparent.

17. The emulsion of claim 16, further comprising an additive which improves transparency.

18. The emulsion of claim 17, wherein the additive is selected from the group consisting of lower alcohols, glycols, and mixtures thereof.

19. The emulsion of claim 17, wherein the additive is present in concentrations ranging from 5 to 30% by weight with respect to the total weight of the emulsion.

20. The emulsion of claim 1, wherein the oil globules have a mean size ranging from 15 to 90 nm.

21. The emulsion of claim 1, further comprising a cosmetic and/or dermatological composition.

22. The emulsion of claim 1, further comprising a water-soluble or fat-soluble cosmetic or dermatological active principle.

23. A composition, comprising the emulsion of claim 1 and a dermatologically acceptable carrier for the dermatological treatment of diseases of the skin, mucous membranes, nails, scalp, and/or hair.

24. A method for cosmetic treatment of the skin, comprising applying a cosmetically effective amount of a composition comprising the emulsion of claim 1 to mucous membranes, nails, scalp, and/or hair.

25. A method for moisturizing the skin, or treating skin which is greasy or sensitive, comprising applying to skin in need thereof an effective skin-treating amount of a composition comprising the emulsion of claim 1.

26. A method for the non-therapeutic treatment of the skin, mucous membranes, nails, scalp, or hair, comprising applying to the skin, mucous membranes, nails, scalp, or hair a non-therapeutic treating amount of a composition comprising the emulsion of claim 1.

27. The emulsion of claim 1, wherein said oil globules comprise an oil selected from the group consisting of liquid petrolatum, liquid fraction of karite butter, sunflower oil, perhydrosqualene, purcellin oil, oil of eucalyptus, oil of lavadin, oil of lavender, oil of vetiver, oil or Litsea cubeba, oil of lemon, oil of sandalwood, oil of rosemary, oil of camomile, oil of savory, oil of nutmeg, oil of cinnamon, oil of hyssop, oil of caraway, oil of orange, oil of geraniol, oil of cade, oil of bergamot, decamethylcyclopentasiloxane, dodecamethylcyclohexasiloxane, perfluoropolyethers, fluoroamines, fluorinatedhydrocarbons, and silicone gums.

28. The emulsion of claim 1, which has been prepared at a temperature of 20 to 45° C.

29. The emulsion of claim 1, which has been prepared at a temperature less than 45° C.

30. The emulsion of claim 1, which has been prepared at a temperature less than 30° C.

31. The emulsion of claim 1, which further comprises a heat-sensitive ingredient.

32. The emulsion of claim 31, wherein said heat-sensitive ingredient is selected from the group consisting of fragrances and vitamins.

33. The emulsion of claim 1, which further comprises vitamin A or retinol palmitate.

34. The emulsion of claim 1, wherein the ratio of the oily phase to the silicone surfactant is from 3 to 6.

* * * * *